United States Patent [19]

Stavinoha

[11] Patent Number: 5,195,356

[45] Date of Patent: Mar. 23, 1993

[54] TEST ASSEMBLY FOR FLUE GAS MONITORS

[75] Inventor: Leroy F. Stavinoha, Needville, Tex.

[73] Assignee: Houston Industries Incorporated, Houston, Tex.

[21] Appl. No.: 728,620

[22] Filed: Jul. 11, 1991

[51] Int. Cl.$^5$ .................................. G01N 21/17
[52] U.S. Cl. .............................. 73/1 G; 356/246
[58] Field of Search ............... 73/1 G, 23.31–23.33; 356/244, 246, 437–442, 243; 250/252.1 R, 252.1 A

[56] References Cited

U.S. PATENT DOCUMENTS

| | | | |
|---|---|---|---|
| 3,773,424 | 11/1973 | Selgin | 356/246 |
| 3,809,913 | 5/1974 | Prellwitz | 356/439 |
| 3,885,162 | 5/1975 | Geertz | 356/243 |
| 4,094,187 | 6/1978 | Navarre, Jr. | |
| 4,205,550 | 6/1980 | Swanson | |
| 4,206,630 | 6/1980 | Powers | |
| 4,279,142 | 7/1981 | McIntyre | |
| 4,322,964 | 4/1982 | Melgaard et al. | |
| 4,445,359 | 5/1984 | Smith | 73/1 G |
| 4,583,859 | 4/1986 | Hall, II | 356/438 |
| 5,003,175 | 3/1991 | Fabinski et al. | 73/1 G |

FOREIGN PATENT DOCUMENTS 0189041  11/1982  Japan .................................. 356/438

Primary Examiner—Robert Raevis
Attorney, Agent, or Firm—Pravel, Gambrell, Hewitt, Kimball & Krieger

[57] ABSTRACT

An assembly is provided for mounting on a flue or exhaust stack conveying combustion gases from a furnace. The assembly permits periodic calibration of a cross-duct flue gas analyzer which senses the flue gas concentrations in the combustion gases. The gas analyzer is calibrated while in place without requiring its removal from service.

10 Claims, 2 Drawing Sheets

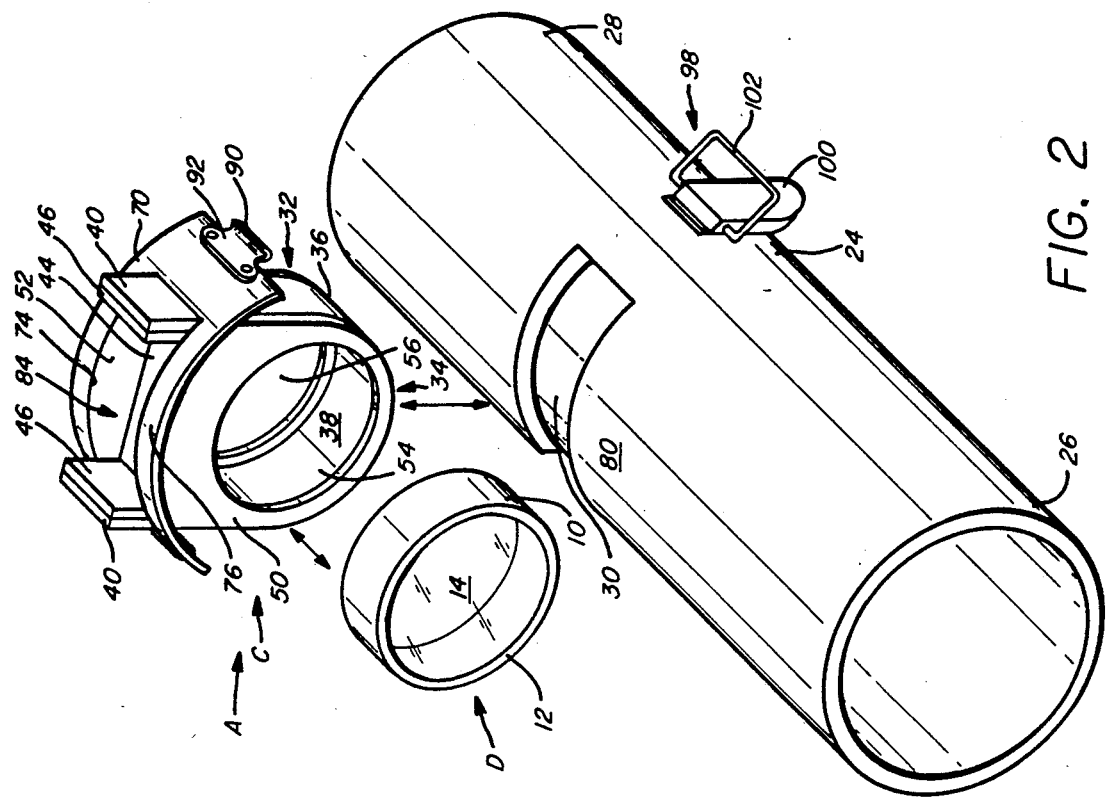
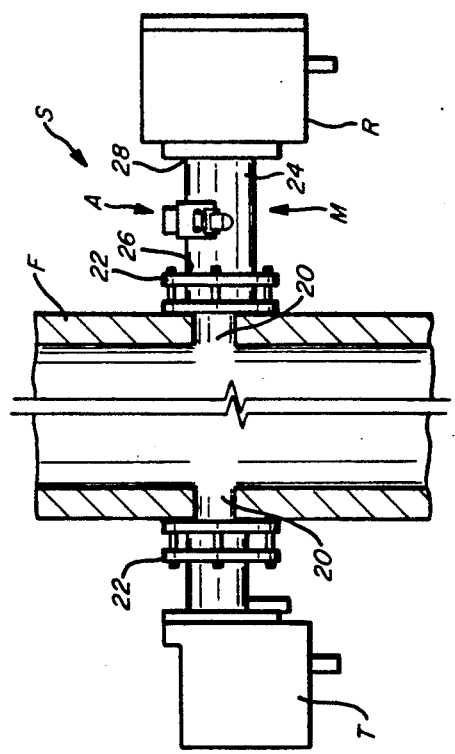

TEST ASSEMBLY FOR FLUE GAS MONITORS

BACKGROUND OF INVENTION

1. Field of Invention

The present invention relates to test assemblies for calibration of gas analyzers.

2. Description of Prior Art

It has been required for environmental reasons, among others, to monitor combustion gases. This is done to determine that the levels of certain constituent gases exiting a flue or stack have been kept within acceptable limits. A common technique used for carbon monoxide level measurement has been an optical monitor using infrared light. A beam of infrared light was sent from an optical transmitter through the exiting gases in the flue to an optical receiving station. The transmitter and receiver were mounted on opposite sides of the gas flue, usually at a fairly elevated position. The amount of carbon monoxide in the exiting flue gases affected the passage of infrared light, and detected variations in light levels thus indicated changing carbon monoxide concentrations.

As time passed, it was necessary to periodically calibrate the monitor. Calibration required that both the transmitter and receiver of the monitor be removed from the flue and taken to a test bench or laboratory for testing. A calibration was then made by placing a sealed disc, containing a known sample concentration of carbon monoxide, between transmitter and receiver. The gas concentration readings could then be checked against the known sample concentration and adjustments made to the monitor electronics as needed.

Prior art patents for gas concentration monitoring, so far as is known, have required that a test probe be inserted into the flue or chamber where gas presence is being analyzed. Examples include U.S. Pat. Nos. 4,094,187; 4,205,550; 4,206,630 and 4,279,142. Calibration of these types of monitors necessitated removal of the test probes from the flues or chambers. A further patent, U.S. Pat. No. 4,322,964, related to a valving arrangement for controlling and regulating flow of both stack gas and calibration gas through a calibration system.

SUMMARY OF INVENTION

Briefly, the present invention provides a new and improved test assembly or jig for mounting a sample disk between on optical test transmitter and receiver of a combustion gas analyzer or monitor. The transmitter and receiver are mounted on a flue or stack through which combustion gasses pass from a furnace or the like. The sample disk contains a known concentration or quantity of a constituent gas of the combustion gases exiting the flue or stack. The assembly includes a disk chamber for receiving the sample disk when calibration of the monitor is to be performed. The disk chamber is mounted between the test transmitter and receiver of the monitor on the flue, permitting in situ calibration of the combustion gas monitor.

BRIEF DESCRIPTION OF THE DRAWINGS

FIG. 1 is an elevation view of a monitor system and test assembly according to the present invention.

FIG. 2 is a partially exploded isometric view of a test assembly portion of the structure of FIG. 1.

DESCRIPTION OF PREFERRED EMBODIMENT

Figure 3:
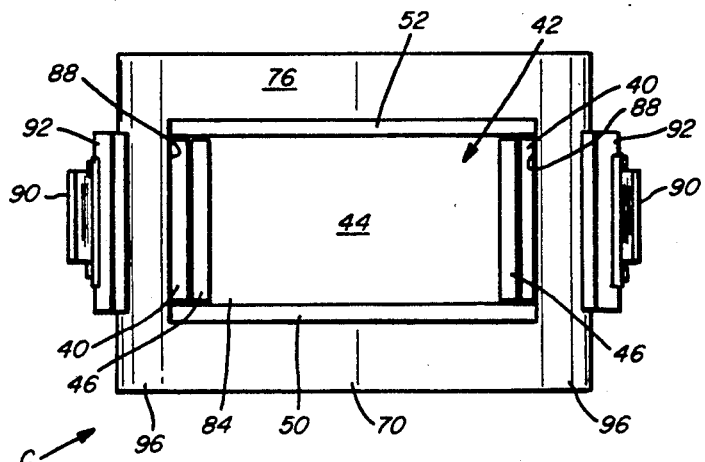
FIG. 3 is a top view of the test assembly of FIG. 2.

In the drawings, the letter S designates generally a monitor system for sensing concentrations of a constituent combustion gas, such as carbon monoxide, in gases exiting a flue or chimney F from a furnace or other combustion chamber. The monitor system S includes an optical transmitter T which sends light beams, typically of infrared light, through the gases in the flue F during their upward passage. The light beams pass through the flue F toward an optical test receiver R which receives such light beams from the transmitter T. The transmitter T and receiver R may be, for example, those of the types sold together as a Land Model 9000 CO Monitor by Land Combustion.

The monitor system S further includes a sample disk D containing a known quantity (usually in parts per million, or ppm) of a constituent combustion gas such as carbon monoxide to be analyzed. The sample disk D is mounted in a disk chamber C by a mounting mechanism M so that the sample disk D is located between the transmitter T and the receiver R of the monitor S.

The sample disk D is a hermetically sealed, generally cylindrically member having a cylindrical body 10 (FIG. 2) with a hollow interior for containing a sample of the constituent combustion gas between ring-shaped end closure members 12 having transparent glass or plastic panes 14 through which the infrared light beams between the transmitter T and the receiver R may pass.

Both the transmitter T and the receiver R are mounted on the flue F adjacent passages or ports 20 (FIG. 1) at a suitable elevation by means of sealed flange fittings 22. A test assembly A of the mounting mechanism M is mounted between one of the flange fittings 22 and either the transmitter T or the receiver R, usually the receiver R.

The test assembly A includes a pipe or support tube 24 of a suitable length mounted with one of the flange fittings 22 on an inner end 26 and with either the transmitter T or receiver R, as the case may be, at an outer end 28.

Figures 4, 5:
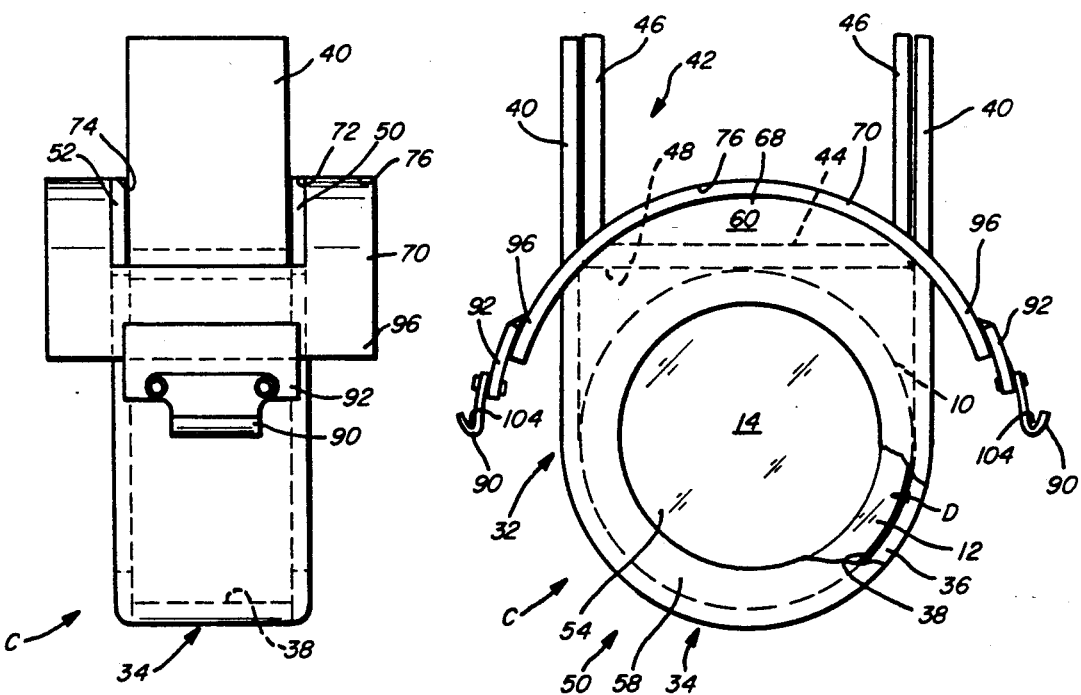
FIGS. 4 is an elevation view of the test assembly of FIG. 2.
FIG. 5 is an elevation view, partly broken away, of the test assembly of FIG. 2.

The pipe 24 includes an insertion port 30 formed therein into which a disk chamber C (FIG. 2) may be inserted. The disk chamber C includes a generally U-shaped yoke member 32 having a central stirrup portion 34 with a cylindrical wall 36 having a cylindrical inner surface 38 into which the cylindrical sample disk D is fitted (FIG. 5). The yoke member 32 includes upwardly extending yoke arms 40 on each side above the stirrup portion 34. The yoke arms 40 extend upwardly a suitable distance beyond the pipe 24 when the disk chamber C is in position (FIGS. 3-5) in the pipe 24.

The disk chamber C further includes a retainer block 42 which has a central plate 44 extending laterally between upwardly extending arms 46. The central plate 44 of the retaining block 42 is adapted to fit snugly on a lower surface 48 (FIG. 5) above the cylindrical body 10 of the sample disk D. If desired, a shock absorbing pad or cushion may be fitted on the surface 48 of the retainer block 42 for snug fitting contact of the sample disk D in the disk chamber C.

The arms 46 of the retainer block 42 and the arms 40 of the yoke member 32 preferably have suitable openings through them into which bolts or other suitable connecting mechanisms may be inserted in order to fixedly mount the retainer block 42 and the yoke member 32 together. In this manner, the retainer block 42 and yoke member 32 of the disk chamber C together function to hold the sample disk D firmly in place in the pipe 24 in the optical path between the transmitter T and the receiver R.

The disk chamber C also includes a front closure plate 50 and a rear closure plate 52 which are fixedly mounted on opposite sides of the stirrup portion 34 of the yoke member 32. The closure plate 50 has a circular opening 54 of corresponding area to the surface area of the transparent pane 14 of the sample disk D, while the closure plate 52 has a like-sized circular opening 56.

The closure plate 50 has a lower semi-circular rim portion 58 of widths substantially equal to the width of stirrup portion 34 and cylindrical body 10 (FIG. 5). The closure plate 52 has a similar sized and shaped lower semi-circular rim portion. An upper portion 60 of the closure plate 50 extends upwardly from the opening 54 to close the spaces within the disk chamber C above the sample disk D and below the surface 48 of central plate 44 of the retainer block 42.

The upper portion 60 of the front closure plate 50 extends further upwardly at a top portion 66 to a semi-circular arcuate surface 68 having a curvature corresponding to an arcuate saddle or curved plate member 70. The closure plate 52 has a similar shaped upper portion to the portion 60 of the front closure plate 50 which also terminates, in this case in an upper surface 74.

The upper surfaces 72 and 74 of the front closure plates 50 and 52 are of the same curvature and of co-planar extent to an upper surface 76 of the curved saddle member 70. The curved saddle member 70 has a curvature equal to that of an upper surface 80 of the pipe member 24 and serves as a portion of the mounting mechanism M to mount the test assembly A to the flue F.

The mounting saddle member 70 has a central passage 84 formed therein through which the yoke arms 40 of the yoke member 32 and the arms 46 of the retainer block 42 extend upwardly. The yoke arms 40 are fixedly mounted with side wall portions 88 (FIG. 3) of the saddle member 70. The retainer block 42 is movable inwardly and outwardly of the central passage 84 in the mounting saddle 70 in order to hold the sample disk D in position.

Connector hooks 90 are mounted extending downwardly from hook straps 92 on side legs 96 of the mounting saddle 70. The connector hooks 90 are adapted to fit into buckle members 98 which are pivotally mounted with buckle fasteners 100 mounted on each side of the pipe member 24. The buckle members 98 are adapted to be rotated upwardly so that central portions 102 thereof may be fitted within slots 104 of the connector hooks 90 in order to firmly hold disk chamber C in place on the pipe 24.

A sealing closure member of like construction to the saddle 70, except having no central passage 84, is provided for mounting with the pipe 24. Such a closure member functions to seal the insertion port 30 in pipe 24 when the test assembly A is not in place in pipe 24.

In the operation of the present invention, the sample disk D is fitted into the yoke member 32 of the disk chamber C and the retainer block 42 mounted in place thereabove. The disk chamber C is then inserted into the insertion port 30 of the pipe 24 until the saddle portion 70 fits against the upper surface 80 of the pipe 24. The buckle members 98 are then pivoted upwardly so that central bar portions 102 may be fitted into the spaces 104 of the connector hooks 90, firmly anchoring the test assembly in position in the optical path between the transmitter T and receiver R. In such a position, light from the transmitter T passes through the transparent plates or panes 14 in the sample disk D. The concentration readings of the constituent combustion gas being monitored by the transmitter T and receiver R of the monitor system S should increase by an amount corresponding to the known concentration quantity of the constituent combustion gas contained inside the sample disk D. In the event that constituent combustion gas readings do not change in this corresponding amount, it is then known that the monitor system S needs testing and calibration. Accordingly, the transmitter T and receiver R may be removed from service and tested as needed. In their place, a new transmitter and receiver may be installed on the flue F. After calibration operations have been finished, the test assembly A may be removed from the pipe 24 and the sealing closure member mounted in place thereof over the port 30 in the pipe 24 to close and seal port 30.

Having described the invention above, various modifications of the techniques, procedures, material and equipment will be apparent to those in the art. It is intended that all such variations within the scope and spirit of the appended claims be embraced thereby.

I claim:

1. An assembly for mounting a calibration sample body, which contains a calibration quantity of a constituent combustion gas, between an optical gas monitor transmitter and receiver transversely and externally to a flue for exiting combustion gases to calibrate the gas monitor, comprising:
    a sample body chamber for receiving the sample body, said sample body chamber comprising:
        a yoke member into which the sample body is fitted;
        front and rear closure plates mounted with said yoke member to form a receptacle for the sample body;
        a retainer block for fitting with said yoke member above the sample body in said receptacle to hold the sample body in place between the transmitter and the receiver;
    support tube means mounting at least one of the optical test transmitter and receiver transversely and externally to the flue;
    means for mounting the sample body chamber in said support tube means between the transmitter and receiver of the gas monitor.

2. The assembly of claim 1, wherein the optical gas monitor transmitter emits light beams along an optical path to the receiver, and wherein:
    said means for mounting comprises means for mounting the sample body chamber in a position locating the sample body in the optical path.

3. The assembly of claim 1, wherein:
    said sample body chamber yoke member has an inner surface into which the sample body is fitted.

4. The assembly of claim 3, wherein the sample body is a cylindrical body, and wherein:
    said inner surface of said yoke member is cylindrical to conform to the cylindrical sample body.

5. The assembly of claim 1, wherein said sample body chamber includes:

yoke arms extending from said yoke member.

6. The assembly of claim 1, wherein:
said sample body chamber includes yoke arms extending from said yoke member;
said retainer block has arms extending therefrom, and further including:
means for mounting said retainer block arms with said yoke arms.

7. The assembly of claim 1, wherein said support tube means comprises:
means mounting the optical gas monitor transmitter to the flue.

8. The assembly of claim 1, wherein said support tube means comprises:
means mounting the optical gas monitor receiver to the flue.

9. The assembly of claim 1, wherein:
said support tube means has an insertion port formed therein; and
said means for mounting comprises means for mounting the sample body in said insertion port of said support tube.

10. A monitor system for sensing concentrations of a constituent combustion gas in gases exiting in a flue with in situ calibration capability, comprising:
an optical test transmitter for sending light beams through the gases in the flue;
an optical test receiver for receiving light beams from the transmitter passing through the flue;
a sample body containing a calibration quantity of a constituent combustion gas;
a sample body chamber for receiving the sample body, said sample body comprising:
a yoke member into which the sample body is fitted;
front and rear closure plates mounted with said yoke member to form a receptacle for the sample body;
a retainer block for fitting with said yoke member above the sample body in said receptacle to hold the sample body in place between the transmitter and the receiver;
support tube means mounting at least one of the optical test transmitter and receiver transversely and externally to the flue;
means for mounting said sample body chamber in said support tube means between said transmitter and receiver of the gas monitor.

* * * * *